United States Patent [19]

Matson

[11] Patent Number: 4,943,668

[45] Date of Patent: Jul. 24, 1990

[54] ALKYLATION OF META-XYLENE WITH ALPHA-OLEFINS

[75] Inventor: Michael S. Matson, Bartlesville, Okla.

[73] Assignee: Phillips Petroleum Company, Bartlesville, Okla.

[21] Appl. No.: 237,818

[22] Filed: Aug. 29, 1988

[51] Int. Cl.$^5$ ............................ C07C 2/66; C07C 2/70
[52] U.S. Cl. ....................................... 585/456; 585/459
[58] Field of Search ................................. 585/456, 459

[56] References Cited

U.S. PATENT DOCUMENTS

| | | | |
|---|---|---|---|
| 4,551,573 | 11/1985 | Cobb | 585/459 |
| 4,599,472 | 7/1986 | Cobb | 585/459 |
| 4,668,835 | 5/1987 | Cobb | 585/459 |

*Primary Examiner*—Patrick P. Garvin
*Assistant Examiner*—E. D. Irzinski
*Attorney, Agent, or Firm*—Richmond, Phillips, Hitchcock & Umphlett

[57] ABSTRACT

A process for producing an alkylated aromatic product having high selectivity to the thermodynamically preferred isomer by contacting meta-xylene and a $C_{13}$ to $C_{20}$ alpha-olefinic compound at a reaction temperature of about 40° to about 80° C. in the presence of a catalyst comprising an aluminum halide and elemental iodine.

29 Claims, No Drawings

ALKYLATION OF META-XYLENE WITH ALPHA-OLEFINS

BACKGROUND OF THE INVENTION

This invention relates to alkylation processes. In another aspect, the invention relates to alkylation of meta-xylene with alpha-olefinic compounds. In a further aspect, the invention relates to the production of alkyl aromatic compounds in high selectivity to the thermodynamically favored aromatic substitution isomer.

Friedel-Crafts, i.e., acid catalyzed alkylation of aromatics, is a well-known reaction. When aromatics are alkylated with an alkyl halide, substantial quantities of hydrogen halide are produced as a by-product of the reaction. Not only are the starting alkyl halides frequently costly and the formation of hydrogen halide as a by-product wasteful, in addition, the by-product hydrogen halide may create a handling and disposal problem due to its corrosive nature. In order to alleviate the above-mentioned problems, aromatics can be alkylated with olefinically unsaturated compounds frequently instead of with alkyl halides. However, prior art reactions of aromatic compounds with olefinically unsaturated compounds frequently suffer from poor selectivity to the preferred isomer of the alkylated aromatic product.

The kinetically favored aromatic substitution isomer, e.g., the kinetically preferred isomer, is predominantly produced when a mild alkylation catalyst and/or mild reaction conditions are used. When the thermodynamically favored aromatic substitution isomer, e.g. the thermodynamically preferred isomer, is the preferred isomer, the alkylation catalyst and reaction conditions required to produce the thermodynamically preferred isomer typically also favor other side reactions such as olefin isomerization, transalkylation and dialkylation.

SUMMARY OF THE INVENTION

It is an object of the invention to provide a process to alkylate meta-xylene with alpha-olefinic compounds to produce alkylated aromatic products having high selectivity to the thermodynamically preferred isomer. It is a further object of the invention to provide a process to produce alkylated aromatic products having high selectivity to the thermodynamically preferred isomer with reduced production of side reaction products compared to prior art processes. It is a further object of the invention to provide a process to produce alkylated aromatic products having high selectivity to the thermodynamically preferred isomer which also has a reduced amount of isomerization of the alpha-olefinic compound.

According to the invention, the alkylated aromatic product having high selectivity to the thermodynamically preferred isomer is prepared by contacting meta-xylene and a $C_{13}$ to $C_{20}$ alpha-olefin at a reaction temperature of about 40° to about 80° C. in the presence of a catalyst comprising an aluminum halide and elemental iodine.

DETAILED DESCRIPTION OF THE INVENTION

Alkylated aromatic compounds produced with a high selectivity to the thermodynamically preferred isomer can be used in a variety of applications. For example, the alkylated aromatic compounds can be sulfonated and used in enhanced oil recovery. A process which enables production of the thermodynamically preferred isomer in high selectivity at mild reaction temperature and relatively short reaction time is economically preferred.

REACTANTS

The process of the present invention comprises contacting meta-xylene and an alpha-olefinic compound. Suitable alpha-olefinic compounds are contemplated to be mono-olefins having the formula

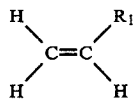

wherein $R_1$ is selected from a $C_{11}$ through $C_{18}$ alkyl radical. Preferred alpha-olefinic compounds are those having $C_{14}$ through $C_{16}$ carbon atoms, i.e. $R_1$ is selected from a $C_{12}$ through $C_{14}$ alkyl radical.

Examples of alpha-olefinic compounds useful in the practice of this invention include 1-tridecene, 1-tetradecene, 1-pentadecene, 1-hexadecene, 1-heptadecene, 1-octadecene, 1-nonadecene and 1-eicosene. The preferred alpha-olefinic compounds are 1-tetradecene and 1-hexadecene.

CATALYST

The catalyst employed in the process of the present invention comprises aluminum halide and elemental iodine. The aluminum halide component can be represented as $$AlX_3$$

wherein each X is independently selected from the halogens. Thus, suitable aluminum halide compounds include aluminum tribromide ($AlBr_3$), dichloroaluminum bromide ($AlCl_2Br$), dibromoaluminum fluoride ($AlBr_2F$), aluminum triiodide ($AlI_3$), aluminum chloride ($AlCl_3$) and the like and mixtures of any two or more thereof. Aluminum chloride is the presently preferred aluminum halide because it is readily available and provides a selective as well as a reactive catalyst.

The catalyst components, i.e. $AlX_3$ and $I_2$, can be combined in any suitable ratio as can be readily determined by one skilled in the art. For purposes of guidance, it is suggested that a molar ratio of elemental iodine to aluminum halide of about 0.005:1 to about 0.5:1 be employed. It is preferred, for most efficient use of reagents, for optimum catalyst performance and for most effective product recovery, that a molar ratio of elemental iodine to aluminum halide of about 0.05:1 to about 0.25:1 be employed.

The catalyst components can be combined in any suitable manner as readily determined by those skilled in the art. Thus, catalyst components can be dry mixed, slurried in the reactant meta-xylene, slurried in an aliquot of the alkylated aromatic product or combined by other suitable techniques.

Although the catalyst can withstand the presence of small amounts of moisture, it is preferred that care be taken to exclude the presence of moisture from the reaction medium. While optional, it is preferred that catalyst preparation as well as the alkylation reaction be carried out in an inert atmosphere, i.e. in the presence of an inert gas such as nitrogen, argon and the like.

REACTION CONDITIONS

The molar ratio of meta-xylene to alpha-olefinic compound employed in the practice of the invention can vary broadly. In order to provide further guidance, it is suggested that a molar ratio of meta-xylene to alpha-olefinic compound of about 1.05:1 to about 4:1 be employed. Molar ratios below the lower value have a tendency to produce undesirable levels of by-products due to multiple alkylation reactions of the aromatic ring, olefin rearrangement and the like, while molar ratios above the upper value provide low product yield based on the amount of starting material employed. Molar ratios of about 1.1:1 to about 1.5:1 are preferred for efficient use of starting materials and minimum formation of by products, which in turn simplifies the task of product recovery.

The alkylation reaction of the invention can be carried out in any suitable vessel which provides efficient contacting between the catalyst components and the reactants. For simplicity, a stirred batch reactor can be employed. The material of construction of the reaction vessel should be chosen so as to be resistant to the possibly corrosive nature of the catalyst. Thus, a glass-lined vessel, or a reaction vessel constructed of Hastelloy C, a trademarked Ni-Cr-Mo alloy of the Cabot Corporation, or other resistant alloys as are known in the art are suitable. The major requirement which any reaction vessel must satisfy is the ability to provide rapid, efficient mixing since the alkylation reaction of the invention catalyzed by $AlX_3$-$I_2$ is frequently a very rapid reaction.

The molar ratio of $AlX_3$ to meta-xylene can be readily determined by those skilled in the art. In order to provide guidance, it is suggested that a molar ratio of about 0.004:1 to about 0.08:1 be employed. Preferably, a molar ratio of about 0.01:1 to about 0.03:1 will be employed for most efficient utilization of reagents.

For the alkylation reaction carried out according to the invention to produce the thermodynamically preferred isomer in high selectivity without producing undesirable by-products, the reaction temperature should be maintained within the range of about 40° to about 80° C. The preferred reaction temperature is about 50° to about 70° C. Any conventional heat exchange equipment for controlling temperature known to those skilled in the art is suitable. In addition, it is convenient to employ excess reactant meta-xylene to control temperature provided the amount of meta-xylene relative to the catalyst or to the alpha-olefinic compound does not exceed the molar ratios set forth above. Use of the alkylated aromatic product as a diluent to control temperature is not desirable since the alkylated aromatic product may undergo undesirable side reactions.

The pressure at which the reaction is carried out is not critical. If the reaction is carried out in a sealed vessel, autogenous pressure is suitable, although higher or lower pressures can be employed. The reaction can also be carried out at atmospheric pressure in an open reaction vessel, in which case the vessel will preferably be equipped with a moisture trap to prevent significant exposure of the catalyst to moisture.

Reaction time is generally quite short and is often dictated by the type of equipment employed. Sufficient time must be provided for thorough contacting of the meta-xylene, the alpha-olefinic compound and the catalyst. Although in theory there is no upper limit as to the reaction time which may be employed, the reaction time is generally about 1 hour to about 2 days. The preferred reaction time will be about 2 hours to about 7 hours. Following completion of the reaction, the reactor contents are cooled and worked up as described in more detail below. The reactor contents can be cooled following addition of all the reactants or the reaction can be allowed to continue for a period of time after addition of the reactants is completed before cooling.

PRODUCTS

The products of the alkylation reaction of the invention have the formula

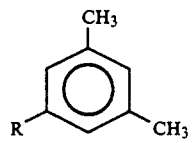

wherein R attaches to the aromatic ring in the position which gives the thermodynamically preferred isomer and wherein R is the alpha-olefinic compound. The alkylated aromatic product is defined as having the R group at the one position on the aromatic ring. For example, the alkylated aromatic product of the invention when 1-hexadecene is the alpha-olefinic compound is 1-hexadecyl-3,5-dimethylbenzene.

In addition to the position in which the alpha-olefinic compound attaches to the aromatic ring, there are positional isomers defined by which carbon atom in the alpha-olefinic compound attaches to the aromatic ring. With 1-hexadecyl-3,5-dimethylbenzene, for example, there are seven positional isomers having the formula

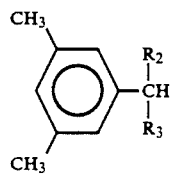

wherein $R_2$ is a $C_1$ to $C_7$ linear alkyl radical, $R_3$ is a $C_8$ to $C_{14}$ linear alkyl radical and the sum of the number of carbon atoms in the $R_2$ and $R_3$ alkyl radicals is 15. The predominant positional isomer has the second carbon atom attached to the aromatic ring. Attachment at the first carbon atom does not occur since the alkylation reaction proceeds through a carbonium ion mechanism. Addition at the other positions, e.g. the third, fourth, etc. carbon atoms on the carbon chain, is the result of isomerization of the double bond of the alpha-olefinic compound. The average position of attachment is referred to as the average carbon number.

The average carbon number is calculated using the following formula $$\text{Average carbon number} = \frac{\sum_{n=2}^{m} n \cdot A_n}{\sum_{n=2}^{m} A_n}$$

wherein n is the number of the positional isomer, $A_n$ is the area % of the n-positional isomer obtained by performing a gas chromatograph analysis of the product and m is the total number of carbon atoms in the alpha-olefin divided by 2. The average carbon number of the alkylated aromatic product is about 2.5 to about 5. The preferred average carbon number of alkylated aromatic product is about 3.6 to about 4.4.

PRODUCT RECOVERY

After completion of the alkylation reaction, the reaction mixture is cooled. The catalyst is then decomposed by treating the reaction mixture with an about 5 to about 10 weight % solution of sodium hydroxide in water. Alternately, the reaction mixture at the completion of the alkylation reaction can be quenched with the same solution of sodium hydroxide in water.

The ratio of wash solution volume to reaction mixture volume should be about 0.2 to about 1.0. After phase separation, the reaction product can be distilled, preferably under moderate vacuum, to insure removal of unreacted meta-xylene and alpha-olefinic compound. During distillation, the temperature should be kept below about 180° C. as prolonged temperatures greater than about 180° C. can cause unwanted transalkylation reactions to occur.

EXAMPLES

Example I

This example describs a series of laboratory runs for the preparation of 1-hexadecyl-3,5-dimethylbenzene as disclosed herein.

In a stirred, 500 mL baffled, glass reaction flask containing an external means for temperature control, catalyst and meta-xylene were charged. The reaction flask was then purged with nitrogen and a continuous nitrogen purge maintained. The contents of the reaction flask were then heated to reaction temperature and the 1-hexadecene slowly added to the reaction flask by means of an addition funnel or a pump.

In a typical run, 60 g (0.565 moles) of meta-xylene, 1.0–2.0 g $AlCl_3$ and 0.2–0.5 g iodine ($I_2$) were charged to the reaction flask. After purging with nitrogen and heating, 94 g (0.417 moles) of 1-hexadecene was added slowly to the reaction flask. After addition of the 1-hexadecene, the reaction flask was allowed to cool. Samples were withdrawn from the reaction flask using a dip tube and analyzed using a Hewlett-Packard HP5880A gas chromatograph, equipped with a 25 meter methylsilicone capillary column, temperature programed from 120° C. (10 minute hold) to 260° C. at 10° C./min. and held at 260° C. fr 25 minutes.

In run 9, a 5 L baffled glass reaction flask was used with a charge of 800 mg (7.54 moles) meta-xylene, 18 g $AlCl_3$, 4 g $I_2$ and 1117 g (4.96 moles) 1-hexadecene and the reaction flask held at 58° C. for 1 hour after addition of the 1-hexadecene was complete.

In runs 7, 8 and 9 and control runs 1–4, the reaction was allowed to continue at reaction temperature for 1–2.2 hours after addition of the 1-hexadecene was completed.

In control runs 1 and 2, the reactions were run at a reaction temperature of 22°–25° C. and in control runs 2, 3 and 4, the catalyst used was $AlCl_3$.

The results of the series of runs are presented in Table I.

TABLE I

| Run No. | moles m-Xylene | moles $AlCl_3$ / moles m-Xylene | moles $I_2$ / moles $AlCl_3$ | Temp., °C. | Reaction Time, hr | m-Xylene Conversion, % | Selectivity[a] 1,3,5-isomer, % | Average Carbon No. |
|---|---|---|---|---|---|---|---|---|
| Control: | | | | | | | | |
| 1a | 0.565 | 0.0162 | 0.138 | 22–25 | 3.22[b] | 68.4 | 53.5 | 3.0 |
| b | | | | " | 4.22 | 68.4 | 60.2 | 3.1 |
| 2a | 0.565 | 0.0161 | 0 | 22–24 | 3.0[b] | 63.3 | 46.5 | 2.9 |
| b | | | | " | 4.0 | 69.5 | 51.8 | 2.9 |
| 3a | 0.565 | 0.0162 | 0 | 55–60 | 3.5[b] | 74.4 | 83.5 | 4.1 |
| b | | | | " | 4.5 | 74.7 | 88.0 | 4.2 |
| 4a | 0.565 | 0.0161 | 0 | 52–62 | 3.22[b] | 77.1 | 85.5 | 4.2 |
| b | | | | " | 4.22 | 77.5 | 91.5 | 4.2 |
| Invention: | | | | | | | | |
| 5 | 0.942 | 0.0159 | 0.105 | 51–55 | 4.43[b] | 28.3 | 92.9 | 3.8 |
| 6a | 0.565 | 0.0159 | 0.131 | 51–52 | 6.55[b] | 74.1 | 89.6 | 4.0 |
| b | | | | 22 | 22.0[c] | 74.1 | 94.1 | 4.0 |
| 7a | 0.377 | 0.0199 | 0.105 | 53–58 | 4.8[b] | 73.3 | 90.8 | 4.3 |
| b | | | | 58–66 | 7.0 | 73.3 | 94.7 | 4.4 |
| 8a | 0.565 | 0.0265 | 0.131 | 49–55 | 4.5[b] | 96.1 | 89.8 | 4.2 |
| b | | | | 52–54 | 6.52 | 96.1 | 93.0 | 4.3 |
| 9a | 7.54 | 0.0179 | 0.117 | 59–63 | 5.75[b] | 66.0 | 92.2 | 4.3 |
| b | | | | 58 | 6.75 | 66.0 | 94.3 | 4.4 |

[a]Selectivity of the 1,3,5-isomer is based only on the 1,2,4- and 1,3,5-monoalkylate isomers but includes all positional isomers in the determination.
[b]Time at which 1-hexadecene addition was completed.
[c]Reaction mixture was cooled and allowed to set overnight.

The results in Table I indicate that conducting the alkylation reaction at 49°–66° C. using an $AlCl_3/I_2$ catalyst gives high selectivity to the thermodynamically preferred isomer. Allowing the reaction mixture to cool and set overnight before decomposition of the catalyst (Run 6b) results in increased selectivity to the thermodynamically preferred isomer. Runs 7b, 8b and 9b indicate that holding the reaction mixture at reaction temperature for 1–2.2 hours after addition of the alpha-olefin is completed, results in increased selectivity to the thermodynamically preferred isomer. Conducting the reaction at 49°–66° C. (Runs 7–9) versus 22°–25° C. (Run 1) results in significant improvement in selectivity to the thermodynamically preferred isomer. Run 5 indicates that high selectivity to the thermodynamically preferred isomer can be obtained even at low conversions of the meta-xylene. Using an $AlCl_3/I_2$ catalyst (Runs 1 and 7–9) versus an $AlCl_3$ catalyst (Runs 2, 3 and 4) indicate that the presence of $I_2$ results in higher selectivities to the thermodynamically preferred isomer.

EXAMPLE II

This example describes a series of laboratory runs for the preparation of 1-hexadecyl-3,5-dimethylbenzene as disclosed herein.

The procedure for runs in Example II was similar to the general procedure for Example I with the following exceptions. A 1 L baffled, glass reaction flask was substituted for the 500 mL baffled, glass reaction flask used in Example I. The 1-hexadecene was charged at ambient temperature (23°-24° C.) over a period of 1.15-1.18 hours and the exothermic nature of the reaction allowed to raise the temperature of the reaction mixture to 74°-75° C.

In Run 14, the addition of 1-hexadecene began at 54° C. and the temperature increased to 90° C. Also in Run 14, the addition of 1-hexadecene was completed in 1.25 hours.

In Run 10, the addition of 1-hexadecene began to 96° C. and the reaction temperature was maintained at 91°-102° C. during the reaction. Also in Run 10, the addition of 1-hexadecene was completed in 1.87 hours.

The results of the series of runs are presented in Table II.

addition, conducting the reaction above the inventive temperature range results in significantly lower selectivity at higher m-xylene conversions (Run 10b and c vs. Runs 11b, 12b, 13b and 14b).

EXAMPLE III

This example describes a series of laboratory runs for the preparation of 1-tetradecyl-3,5-dimethylbenzene as disclosed herein.

The procedure and apparatus for runs in Example III was very similar to the general procedure for Example I with the following exceptions.

In control run 15, the reaction mixture was not heated prior to addition of the 1-tetradecene and the reaction temperature was maintained at ambient temperature.

In control run 16, the reaction mixture of control run

TABLE II

| Run No. | moles m-Xylene | moles $AlCl_3$ moles m-Xylene | moles $I_2$ moles $AlCl_3$ | Temp., °C. | Reaction Time, hr | m-Xylene Conversion, % | Selectivity[a] 1,3,5-isomer, % | Average Carbon No. |
|---|---|---|---|---|---|---|---|---|
| Control: | | | | | | | | |
| 10a | 0.565 | 0.0162 | 0.138 | 91-96 | 1.87[b] | 84.4 | 64.1 | 4.3 |
| b | | | | 94-102 | 6.36[c] | 87.7 | 70.4 | 4.4 |
| c | | | | 23 | ~24 | 87.7 | 72.2 | 4.4 |
| Invention: | | | | | | | | |
| 11a | 1.649 | 0.0136 | 0.175 | 23-74 | 1.15[b] | 84.8 | 86.8 | 4.1 |
| b | | | | 74-79 | 6.2 | 84.8 | 93.7 | 4.3 |
| 12a | 1.649 | 0.0091 | 0.173 | 23-74 | 1.18[b] | 83.8 | 82.2 | 4.0 |
| b | | | | 69-76 | 7.27 | 83.8 | 91.9 | 4.2 |
| 13a | 1.649 | 0.0114 | 0.105 | 24-75 | 1.18[b] | 84.4 | 85.6 | 4.1 |
| b | | | | 72-80 | 5.18 | 84.4 | 93.0 | 4.3 |
| 14a | 1.649 | 0.0136 | 0.175 | 54-90 | 1.25[b] | 83.8 | 81.6 | 4.5 |
| b | | | | 71-76 | 6.13 | 83.8 | 91.7 | 4.6 |

[a]Selectivity of the 1,3,5-isomer is based only on the 1,2,4- and 1,3,5-monoalkylate isomers but includes all positional isomers in the determination.
[b]Time at which 1-hexadecene addition was completed.
[c]At end of reaction, 0.0038 moles of $AlCl_3$ was added to the reactor and the reaction mixture was cooled and allowed to set overnight.

The results in Table II indicate that the alpha-olefinic compound can be charged to the meta-xylene/catayst mixture over a shorter time period at ambient temperature and the reaction temperature allowed to increase via the heat of reaction to the desired reaction temperature without detrimentally effecting the selectivity to the thermodynamically preferred isomer (Runs 11-13). Charging the alpha-olefinic compound over a shorter time period at an elevated temperature and allowing the heat of reaction to increase the reactor temperature above the inventive temperature range does not have a significantly detrimental effect on the selectivity to the thermodynamically preferred isomer provided the reaction temperature is controlled within the inventive temperature range (Run 14). Runs 11-14 also indicate that an extended hold time after the final meta-xylene conversion has been attained does not have a detrimental effect on the average carbon number. In addition, a higher loading of $AlCl_3$ with equivalent molar ratio of $I_2$ to $AlCl_3$ (Run 11b vs. Run 12b) results in better selectivity to the thermodynamically preferred isomer. In 16 was heated to 54° C. and held for an additional 5 hours.

The results of the series of runs are presented in Table III.

TABLE III

| Run No. | moles m-Xylene | moles $AlCl_3$ moles m-Xylene | moles $I_2$ moles $AlCl_3$ | Temp., °C. | Reaction Time, hr[b] | m-Xylene Conversion, % | Selectivity[a] 1,3,5-isomer, % | Average Carbon No. | % Dialkylate |
|---|---|---|---|---|---|---|---|---|---|
| Control: | | | | | | | | | |
| 15 | 0.64 | 0.0164 | 0.113 | 20-24 | 5.0 | 82 | 54 | 2.4 | 9.1 |
| 16[c] | 0.64 | 0.0164 | 0.113 | 54 | 5.0 | 90 | 87 | 3.2 | 3.1 |
| Invention: | | | | | | | | | |
| 17 | 0.942 | 0.0159 | 0.105 | 50-55 | 6.0 | 32 | 94 | 2.9 | —[d] |
| 18 | 0.942 | 0.0159 | 0.105 | 60 | 6.45 | 77 | 84 | 3.8 | 0.5 |

[a]Selectivity of the 1,3,5-isomer is based only on the 1,2,4- and 1,3,5-monoalkylate isomers but includes all positional isomers in the determination.
[b]The reaction was stopped when the 1-tetradecene addition was completed.
[c]Run 16 is a continuation of Run 15 in which the reaction temperature was increased and the reaction allowed to proceed for an additional 5 hours.
[d]not detected.

The results in Table III indicate that a lower reaction temperature results in the increased formation of undesirable dialkylate even when the lower temperature is increased and the reaction allowed to proceed (Runs 15 and 16 vs. Runs 17 and 18). In addition, the selectivity to the thermodynamically preferred isomer is also lower for alkylations done at temperatures below the inventive temperature range (Run 15 v. Runs 17 and 18).

EXAMPLE IV

This example describes a series of pilot plant runs for the preparation of 1-hexadecyl-3,5-dimethylbenzene as disclosed herein.

To a stirred 100-gallon batch reactor containing a means for temperature control, the $AlCl_3$ and $I_2$ were slurried in 5 gallons of meta-xylene and charged. The remainder of the meta-xylene was charged and the reactor heated to 45° C. with stirring at 200 rpm. The reactor was purged with nitrogen and nitrogen was maintained to control reactor pressure. The 1-hexadecene was then charged at approximately 2 lbs/minute with the total amount being charged in 2-2.25 hours. During addition of the 1-hexadecene, the reaction temperature was allowed to increase to 55°-60° C. and this temperature was maintained for 4 hours. The catalyst was neutralized by washing with 250 lbs of an aqueous 5% NaOH solution with stirring at 200 rpm for 30 minutes. The phases were allowed to settle for 30 minutes and the water phase removed. Excess meta-xylene was initially distilled off at 115° C. under vacuum. The batch was subsequently treated by heating to 170° C. at atmospheric pressure and sparging nitrogen through the liquid at a rate of about 600-700 scfh for 3-4 hours. This recovery procedure reduced the level of meta-xylene in the product to less than 0.1%.

The results of the series of runs are presented in Table IV.

TABLE IV

| Run No. | moles m-Xylene | moles AlCl$_3$ moles m-Xylene | moles I$_2$ moles AlCl$_3$ | Temp., °C. | Reaction Time, hr[b] | m-Xylene Conversion, % | Selectivity[a] 1,3,5-isomer, % | Average Carbon No.[c] |
|---|---|---|---|---|---|---|---|---|
| Invention: | | | | | | | | |
| 19[d] | 2.05 | 0.0157 | 0.134 | 55-60 | 6.17 | 42 | 94.7 | 4.0 |
| 20[d] | 2.05 | 0.0157 | 0.134 | 55-60 | 6.01 | 49 | 94.7 | 4.2 |
| 21[d] | 2.05 | 0.0157 | 0.134 | 55-60 | 6.25 | 64 | 94.4 | 3.9 |

[a]Selectivity of the 1,3,5-isomer is based only on the 1,2,4- and 1,3,5-monoalkylate isomers but includes all positional isomers in the determination.
[b]Reaction time includes 2.01-2.25 hours for addition of 1-hexadecene followed by a 4 hour hold time.
[c]The average carbon number was determined after 2 hours of the 4 hour hold time.
[d]The reactor samples were analyzed according to the method set forth in Example I.

The results in Table IV indicate that the inventive process (Runs 19, 20 and 21) is operable on a pilot plant scale in equipment that is similar to that which would be used in a commercial process.

While this invention has been described in detail for the purpose of illustration, it is not to be construed as limited thereby but is intended to cover all changes and modifications within the spirit and scope thereof.

That which is claimed is:

1. A process for producing an alkylated aromatic product consisting essentially of a $C_{13}$-$C_{20}$ monoalkylated meta-xylene wherein the 1,3,5 isomer predominates the 1,2,4 isomer, said process comprising gradually adding a $C_{13}$ to $C_{20}$ α-olefinic compound to a mixture of meta-xylene and a catalyst system while allowing the reaction temperature to rise to a level in the range of about 40° C. to about 80° C., then maintaining a reaction temperature in the range of 40° C. to about 80° C. for a suitable period of time after the addition of the olefinic compound has been completed, wherein said catalyst system comprises elemental iodine and $AlX_3$ wherein each X is independently selected from the halogens.

2. A process according to claim 1 wherein said $AlX_3$ is $AlCl_3$.

3. A process according to claim 2 wherein the molar ratio of said elemental iodine to said $AlCl_3$ is about 0.05:1 to about 0.5:1.

4. A process according to claim 3 wherein the molar ratio of said $AlCl_3$ to said meta-xylene is about 0.004:1 to about 0.08:1.

5. A process according to claim 4 wherein the molar ratio of said meta-xylene to said alpha-olefinic compound is in the range of about 1.05:1 to about 4:1.

6. A process according to claim 5 wherein said olefinic compound is gradually added to said mixture while allowing the reaction temperature to rise to a level in the range of about 50° C. to about 70° C., then maintaining a reaction temperature in the range of 50° C. to about 70° C. for a suitable period of time.

7. A process according to claim 6 wherein after having been maintained at said reaction temperature in the range of 50° C. to about 70° C. for said suitable period of time the resulting reaction mixture is contacted with a 5 to 10 weight percent solution of sodium hydroxide.

8. A process according to claim 7 wherein after the reaction mixture is contacted with the aqueous sodium hydroxide the resulting aqueous phase is separated from the organic phase and then the organic phase is subjected to distillation at a temperature below 180° C. to remove unreacted meta-xylene and unreacted α-olefin.

9. A process according to claim 2 wherein after having been maintained at said reaction temperature in the range of 50° C. to about 70° C. for said suitable period of time the resulting mixture is contacted with a 5 to 10 weight percent solution of sodium hydroxide.

10. A process according to claim 9 wherein after the reaction mixture is contacted with the aqueous sodium hydroxide the resulting aqueous phase is separated from the organic phase and then the organic phase is subjected to distillation at a temperature below 180° C. to remove unreacted meta-xylene and unreacted α-olefin.

11. A process according to claim 2 which produces an alkylated aromatic product substantially free of dialkylated meta-xylene.

12. A process according to claim 2 wherein said α-olefinic reactant is 1-hexadecene.

13. A process according to claim 2 wherein said α-olefinic reactant is 1-tetradecene.

14. A process for producing an alkylated aromatic product consisting essentially of hexadecyl-substituted meta-xylene wherein the molar ratio of 1-hexadecyl-3,5-dimethylbenzene to 1-hexadecyl-2,4-dimethylbenzene is at least about 6.576:1 comprising gradually adding 1-hexadecene to a mixture of meta-xylene and a catalyst system while allowing the reaction temperature to rise to a level in the range of about 40° C. to about 80° C., then maintaining a reaction temperature in the range of 40° C. to about 80° C. for a suitable period of time, wherein said catalyst system comprises elemental iodine and $AlX_3$ wherein each X is independently selected from the halogens.

15. A process according to claim 14 wherein $AlX_3$ is $AlCl_3$.

16. A process according to claim 15 which produces an alkylated aromatic product wherein the average carbon number of said hexadecyl-substituted meta-xylene is in the range of about 3.8 to about 4.4.

17. A process according to claim 16 which produces a product wherein the molar ratio of 1-hexadecyl-3,5- dimethylbenzene to 1-hexadecyl-2,4-dimethylbenzene is at least about 10:1.

18. A process according to claim 15 which produces a product wherein the molar ratio of 1-hexadecyl-3,5-dimethylbenzene to 1-hexadecyl-2,4-dimethylbenzene is at least about 10:1.

19. A process according to claim 18 which produces an alkylated aromatic product wherein the average carbon number of said hexadecyl-substituted meta-xylene is at least about 4.

20. A process according to claim 15 which produces an alkylated aromatic product wherein the average carbon number of said hexadecyl-substituted meta-xylene is at least about 4.

21. A process according to claim 15 wherein the molar ratio of said elemental iodine to said $AlCl_3$ is about 0.005:1 to about 0.5:1, the molar ratio of said $AlCl_3$ to said meta-xylene is about 0.004:1 to about 0.008:1, and the molar ratio of said meta-xylene to said 1-hexadecene is about 1.05:1 to about 4:1.

22. A process according to claim 21 wherein after having been maintained at said reaction temperature in the range of 40° C. to about 80° C. for said suitable period of time the resulting reaction mixture is contacted with a 5 to 10 weight percent aqueous solution of sodium hydroxide.

23. A process according to claim 22 wherein the resulting aqueous phase is separated from the organic phase and then the organic phase is subjected to distillation at a temperature below 180° C. to remove unreacted meta-xylene and unreacted 1-hexadecene.

24. A process for producing an alkylated aromatic product consisting essentially of mono-alkylated meta-xylene wherein the 1,3,5 isomer predominantes the 1,2,4 isomer comprising contacting
    (a) meta-xylene; and
    (b) a $C_{13}$–$C_{20}$ α-olefin at a reaction temperature in the range of about 40° C. to about 80° C. in the presence of a catalyst comprising elemental iodine and $AlX_3$ wherein each X is independently selected from the halogens.

25. A process according to claim 24 wherein said $AlX_3$ is $AlCl_3$.

26. A process according to claim 24 wherein said α-olefin is 1-hexadecene.

27. A process according to claim 25 wherein said α-olefin is 1-tetradecene.

28. A process according to claim 26 which produces an aromatic product consisting essentially of hexadecyl-substituted meta-xylene wherein the molar ratio of 1-hexadecyl-3,5-dimethylbenzene to 1-hexadecyl-2,4-dimethylbenzene is at least about 10:1.

29. A process according to claim 28 wherein the average carbon number of said hexadecyl-substituted meta-xylene is in the range of about 3.8 to 4.4.

* * * * *